United States Patent
Runge et al.

(10) Patent No.: US 6,261,598 B1
(45) Date of Patent: Jul. 17, 2001

(54) CAROTENOID FORMULATIONS, COMPRISING A MIXTURE OF B-CAROTENS, LYCOPENE AND LUTEIN

(75) Inventors: Frank Runge, Maxdorf (DE); Jan Holm-Hansen, Alleroed; Birgit Michelsen, Thurovej, both of (DK)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/382,772

(22) Filed: Aug. 25, 1999

(30) Foreign Application Priority Data

Aug. 26, 1998 (DE) ............................................... 198 38 636

(51) Int. Cl.⁷ ............................... A61K 9/64; A61K 9/48; A61K 47/00; A23K 1/165; A01N 25/00
(52) U.S. Cl. ........................ 424/456; 424/401; 424/489; 424/442; 424/451; 514/773; 514/779; 514/781; 514/784; 514/785
(58) Field of Search ................................... 424/401, 451, 424/456, 439, 442; 514/781, 784, 785, 779, 773

(56) References Cited

U.S. PATENT DOCUMENTS

| | | | |
|---|---|---|---|
| 4,182,731 | 1/1980 | Schulz et al. | 260/606 |
| 4,435,427 | 3/1984 | Hoppe et al. | 424/356 |
| 5,166,445 | 11/1992 | Meyer | 568/2 |
| 5,180,717 * | 1/1993 | Matsuda et al. | 514/681 |
| 5,208,381 | 5/1993 | Meyer | 568/10 |
| 5,350,773 | 9/1994 | Schweikert et al. | 514/763 |
| 5,364,563 | 11/1994 | Cathrein et al. | 252/311 |
| 5,382,714 * | 1/1995 | Khachik | 568/834 |
| 5,453,447 | 9/1995 | End et al. | 514/763 |
| 5,648,564 | 7/1997 | Ausich et al. | 568/834 |

FOREIGN PATENT DOCUMENTS

| | | |
|---|---|---|
| 498824 | 8/1992 | (EP) . |
| 96/19215 | 6/1996 | (WO) . |
| 96/19217 | 6/1996 | (WO) . |
| 97/15554 | 5/1997 | (WO) . |
| 97/48287 | 12/1997 | (WO) . |

OTHER PUBLICATIONS

Solgar "Lutein Lycopene Carotene Complex Vegicaps", XP002125651 (online reference); Mar. 3, 1998.
Naturmed Essentials "Eye factors", XP002125652 (online reference); Jul. 15, 1998.
ONCCOR "Simone Protective Healthcare", XP002125653 (online reference); Mar. 16, 1998.
"Betatene–Mixed Carotenoids the body Needs", XP002125654 (online reference); Aug. 21, 1997.
Webvitamins "Twinlab Multi Vitamins and Minerals" XP002125655 (online reference); Aug. 24, 1998.
Solgar Online Reference "Advanced Carotinois Complex Softgels" XP002125656 (online reference); Apr. 7, 1997.
VERIS "Typical Carotenoid Content of Selected Fruits and Vegetables", XP002125657 (online reference); Mar. 3, 1998.
Sogar "Lutein Lycopene Carotene Complex Vegicaps" XP002125651, Mar. 1998.*
Nebeling et al., *J. Amer. Dietetic Assoc.*, 97(9), 1997, 991–996.

* cited by examiner

Primary Examiner—Thurman K. Page
Assistant Examiner—S. Tran
(74) Attorney, Agent, or Firm—Keil & Weinakuf

(57) ABSTRACT

Carotenoid formulations comprising a mixture of β-carotene, lycopene and lutein, and the use thereof in human and animal foods, cosmetics and pharmaceuticals.

9 Claims, No Drawings

CAROTENOID FORMULATIONS, COMPRISING A MIXTURE OF B-CAROTENS, LYCOPENE AND LUTEIN

Carotenoid formulations, comprising a mixture of β-carotene, lycopene and lutein The invention relates to carotenoid formulations comprising a mixture of β-carotene, lycopene and lutein.

Carotenoids form a group of pigments which have a yellow or red color, are widespread in nature and confer the characteristic colors on many foodstuffs.

Epidemiological studies have moreover shown that frequent and regular consumption of carotenoid-containing fruit and vegetables reduces the risk of chronic disorders, including cardiovascular disorders, and has a beneficial effect on cancer prevention.

This protective function of the carotenoids is seen both in their action as antioxidants and, as in the case of β-carotene, in their provitamin A activity.

There is particular interest in this connection in the three carotenoids β-carotene, lycopene and lutein, which occur widely in foodstuffs such as, for example, tomatoes, carrots, spinach, paprika and broccoli [see Journal of the American Dietetic Association, 97(9), 991–996 (1997)]. In particular, the mixture of these three carotenoids represents a system with particular antioxidant properties.

This is why nutritionists recommend additional, preventive intake of antioxidant vitamins and carotenoids. The food and drugs market therefore offers consumers a large number of such "cytoprotective products".

Formulations for food products or food supplements which specifically comprise a combination of β-carotene, lycopene and lutein in high concentrations and high purity have, however, not been disclosed to date.

Thus, lycopene is obtainable, for example, under the name Lyc-O-Mato® (from LycoRed, Israel) as a 6% strength oily dispersion. According to WO 97/48287 it is extracted as natural carotenoid from tomatoes. Because of the high phospholipid content in Lyc-O-Mato®, together with a high viscosity of the oily dispersion, the use properties of this formulation are not always satisfactory. In particular, the use of Lyc-O-Mato® is unsatisfactory for producing high-concentration carotenoid-containing gelatin capsules.

U.S. Pat. No. 5,382,714 and U.S. Pat. No. 5,648,564 describe processes for isolating lutein from the oily extract from marigolds, and the use of the lutein obtained in this way as food color and as antioxidant in cancer prophylaxis. These patents provide no pointers to combinations of β-carotene, lycopene and lutein.

It is an object of the present invention to provide stable formulations of a ternary combination of carotenoids consisting of β-carotene, lycopene and lutein which do not have the abovementioned prior art disadvantages.

We have found that this object is achieved by carotenoid formulations comprising a mixture of β-carotene, lycopene and lutein.

The term "carotenoid formulations" means for the purpose of this invention both solutions, solubilizates and dispersions, such as emulsions and suspensions, and dry carotenoid powders produced therefrom. Preferred formulations are dispersions, such as emulsions and suspensions, in particular oil-containing suspensions.

The ratio of the amounts of the carotenoids present in the mixture is 1 part of β-carotene, 0.05 to 20 parts of lycopene and 0.05 to 20 parts of lutein, preferably 1 part of β-carotene, 0.1 to 5 parts of lycopene and 0.1 to 5 parts of lutein, particularly preferably 1 part of β-carotene, 0.2 to 2 parts of lycopene and 0.1 to 2 parts of lutein, very particularly preferably 1 part of β-carotene, 0.3 to 1.2 parts of lycopene and 0.1 to 0.5 part of lutein.

The content of β-carotene, lycopene and lutein in the form of the combination according to the invention in the formulations is generally between 0.1 and 40% by weight, preferably between 5 and 35% by weight, particularly preferably between 10 and 33% by weight, very particularly preferably between 15 and 32% by weight, based on the total amount of the formulation.

The carotenoid formulations are further distinguished by having a phosphorus content of less than 2.0% by weight, advantageously less than 1.0% by weight, preferably less than 0.5% by weight, particularly preferably less than 0.1% by weight, very particularly preferably less than 0.02% by weight, based on the total amount of the mixture of β-carotene, lycopene and lutein.

The low phosphorus content is at the same time associated with a low content of phospholipids, which improves the use properties of the formulations, such as, for example, the flowability of oil-containing dispersions, especially at low temperatures. The dispersants according to the invention have such a low viscosity even at temperatures between 5° C. and 40° C. that it is possible to dispense with heating the carotenoid dispersion (to reduce the viscosity) during further processing, e.g. during filling into gelatin capsules. This means that it is possible to avoid unwanted losses of activity through chemical or thermal breakdown of the carotenoids.

The carotenoids used to produce the formulations are preferably employed in the form of their crystals with a purity exceeding 75%, preferably exceeding 90%, particularly preferably exceeding 95%, very particularly preferably exceeding 98%. It is moreover possible to employ β-carotene, lycopene and lutein from natural sources as well as, preferably, synthetically prepared carotenoids, in particular synthetically prepared β-carotene and lycopene. Thus, for example, the β-carotene or lycopene used can be obtained by one of the processes disclosed in EP-A-382067 or EP-A-000140.

Besides the abovementioned mixture of β-carotene, lycopene and lutein, the carotenoid formulations according to the invention can contain at least one other active substance in concentrations of 0.01 to 40% by weight, preferably 0.1 to 30% by weight, particularly preferably in concentrations of 0.5 to 20% by weight.

Possible examples of these active substances are the following:

Other carotenoids such as for example bixin, zeaxanthin, cryptoxanthin, citranaxanthin, canthaxanthin, β-apo-4-carotenal, β-apo-8-carotenal, β-apo-8-carotenoic esters, astaxanthin, singly or as mixture.

Vitamins, e.g. vitamin A, vitamin A acetate, vitamin A palmitate, riboflavin, vitamin $B_{12}$, ascorbic acid, ascorbyl palmitate, nicotinic acid, nicotinamide, pyridoxine hydrochloride, vitamin $D_3$, tocopherol, tocopherol acetate, tocopherol palmitate, tocotrienol, vitamin K, thiamine, calcium pantothenate, biotin, lipoic acid, folic acid, folic acid derivatives such as tetraBASF hydrofolic acid, 5-methyltetrahydrofolic acid, 10-formyltetrahydrofolic acid or 5-formyltetrahydrofolic acid.

Compounds with vitamin or coenzyme characteristics, e.g. choline chloride, carnitine, taurine, creatine, ubiquinones, S-methylmethionine, S-adenosylmethionine.

Polyunsaturated fatty acids, e.g. linoleic acid, linolenic acid, arachidonic acid, eicosapentaenoic acid, docosahexaenoic acid.

Garlic constituents, e.g. diallyl thiosulfinate, S-allylcysteine sulfoxide, vinyldithiines, ajoene.

Allithiamines such as benfotiamine, fursultiamine, octotiamine or bentiamine.

Glutathione and its esters such as, for example GSH monomethyl ester, GSH dimethyl ester, GSH monoethyl ester, GSH diethyl ester.

Depending on the nature of the formulation, it may contain, besides the carotenoids, at least one other ancillary substance or additive such as, for example, oils, protective colloids, plasticizers, antioxidants and/or emulsifiers.

In the case of a dispersion, especially in the case of a suspension or an emulsion, it is advantageous to use in addition a physiologically acceptable oil such as, for example, sesame oil, corn oil, cottonseed oil, soybean oil or peanut oil, esters of medium chain-lengths vegetable fatty acids and, in addition, fish oils such as, for example, mackerel, sprat or salmon oil.

Examples of protective colloids used are gelatin, fish gelatin, starch, dextrin, plant proteins, pectin, gum arabics, casein, caseinate or mixtures thereof. However, it is also possible to employ polyvinyl alcohol, polyvinylpyrrolidone, methylcellulose, carboxymethylcellulose, hydroxypropylcellulose and alginates. For further details, reference is made to R. A. Morton, Fat Soluble vitamins, Intern. Encyclopedia of Food and Nutrition, Vol. 9, Pergamon Press 1970, pages 128–131. To increase the mechanical stability of, for example, the dry powder, it is expedient to add to the colloid a plasticizer such as sugars or sugar alcohols, e.g. sucrose, glucose, lactose, invert sugar, sorbitol, mannitol or glycerol.

The ratio of protective colloid and plasticizer to carotenoid is generally chosen so that the final product is a formulation which, besides the abovementioned carotenoids, contains 10 to 50% by weight of a protective colloid, 20 to 70% by weight of a plasticizer, all percentage data based on the dry weight of the formulation, and, where appropriate, minor amounts of a stabilizer.

To increase the stability of the active substance against oxidative degradation, it is advantageous to add stabilizers such as $\alpha$-tocopherol, butylated hydroxytoluene, butylated hydroxyanisole, ascorbic acid or ethoxyouines.

Emulsifiers or solubilizers which can be used in the case of emulsions and dry powders produced therefrom, and in the case of solubilizates are, for example, ascorbyl palmitate, polyglycol fatty acid esters, sorbitan fatty acid esters, propylene glycol fatty acid esters or lecithin in a concentration of from 0 to 200% by weight, preferably 10 to 150% by weight, particularly preferably 20 to 80%, based on the carotenoids.

The carotenoid formulations are produced in a manner known per se. Thus, for example, solubilizates or emulsions can be produced as disclosed in EP-A-0 055 817 or EP-0 479 066 and EP-A-0 551 638. The production of carotenoid dispersions and conversion thereof into a dry powder is described, inter alia, in EP-A-0 498 824 and EP-A-0 410 236.

The preferred oil-containing carotenoid dispersions can be produced in a manner known per se, for example by grinding the crystalline carotenoids in a physiologically acceptable oil using a ball mill.

The carotenoid formulations are suitable inter alia as additive for coloring food products, in particular beverage products, as agent for producing pharmaceutical and cosmetic preparations, and for producing food supplement products for humans and animals.

In principle, all the abovementioned types of formulation are suitable for the use of the carotenoid formulations according to the invention for coloring foodstuffs. Thus, beverages can be colored by using, for example, emulsions, solubilizates or else water-dispersible dry powders comprising mixtures of $\beta$-carotene, lycopene and lutein in the concentrations mentioned above.

The oil-containing dispersions also have, even in low concentrations, a strong coloring power. They are suitable for coloring oils and fats, and foodstuffs such as margarine, butter, cheese products, icecream, soups, sauces and egg products by addition to the oily phase.

However, it is also possible to add dry powders which contain the carotenoid combinations according to the invention to dairy products such as yoghurt, milk drinks or milk ice, and blancmange powders, baking mixes and confectionary, for example fruit gums.

The invention also relates to food supplements, animal feedstuffs, human foodstuffs and pharmaceutical and cosmetic preparations comprising the carotenoid formulations of mixtures of $\beta$-carotene, lycopene and lutein, described above.

Food supplement products and pharmaceutical preparations comprising the carotenoid mixture according to the invention mean, inter alia, uncoated and coated tablets, and hard and soft gelatin capsules. Preferred food supplement products are soft gelatin capsules in which the carotenoids are present as oil-containing suspension. The carotenoid content in these capsules is in the range from 0.5 to 20 mg of $\beta$-carotene, 0.5 to 20 mg of lycopene and 0.5 to 20 mg of lutein, preferably in the range from 1 to 15 mg of $\beta$-carotene, 1 to 15 mg of lycopene and 1 to 10 mg of lutein, particularly preferably in the range from 2 to 10 mg of $\beta$-carotene, 2 to 10 mg of lycopene and 1 to 5 mg of lutein.

Cosmetic preparations, for example preparations for topical application, such as creams and lotions, comprise the carotenoid formulations according to the invention preferably in the form of emulsions; oral cosmetic preparations such as, for example, coated tablets may likewise contain the carotenoids as oil-containing suspension.

The following examples explain the production of the formulations according to the invention in detail.

EXAMPLE 1

Production of an oil-containing $\beta$-carotene/lycopene/lutein dispersion 350 g of crystalline $\beta$-carotene, 180 g of crystalline lycopene and 70 g of crystalline lutein and 25 g of a-tocopherol were stirred into 1850 g of a medium chain-length triglyceride (Delios® SK supplied by Grünau). Stirring was continued with a paddle stirrer until a homogeneous suspension was obtained. The mixture was transferred into a stirrable receiver from which the suspension was conveyed by a peristaltic pump through a continuously operated Dyno Mill KDL special ball mill, whose grinding containers were charged with 480 g of Dragonit 25 (diameter 850–1230 $\mu$m) grinding particles. The agitator shaft rotated at 4500 rpm. The fine suspension emerging from the mill was collected. The average particle size was about 15 $\mu$m.

EXAMPLE 2

Production of an oil-containing $\beta$-carotene/lycopene/lutein dispersion 100 g of a 30% by weight $\beta$-carotene dispersion (Lucarotin® 30 M from BASF), 50 g of a 20% by weight lutein dispersion (FloraGLO® 20 from Kemin) and 100 g of a 10% by weight lycopene dispersion in corn oil (produced in a Dyno-Mill with 0.6–0.8 mm glass beads as grinding particles) were vigorously mixed in a beaker at room temperature using a laboratory stirrer.

EXAMPLE 3

Production of a β-carotene/lycopene/lutein solubilizate

A suspension of 150 g of crystalline β-carotene, 50 g of crystalline lycopene and 25 g of crystalline lutein in 2500 g of polyoxyethylene(20)sorbitan monostearate (Tween® 60) which had been preheated to 65° C. was fed at a rate of 2.2 kg/h into a heating coil which had an internal diameter of 2 mm and a length of 12 m and which was immersed in an oil bath kept at 190° C. At a temperature of 164° C. after emerging from the heat exchanger, and after a residence time of 62 s, the carotenoid mixture was dissolved in the emulsifier. In a subsequent mixing chamber (details of the apparatus are to be found in the description in EP-A-0 479 066), the carotenoid solution underwent turbulent mixing with water at 25° C. (throughput: 5.4 kg/h) at a mixing temperature of 62° C. The solubilizate was discharged under a pressure of 20 bar through a pressure-controlling valve. A dark red, micellar carotenoid solution with a carotenoid content (β-carotene, lycopene and lutein in the ratio 1:0.33:0.17) of 2.0% by weight and a micelle size of 20 nm was obtained.

EXAMPLE 4

Production of a β-carotene/lycopene/lutein emulsion a) 56 g of distilled water and 5.6 g of 3-molar sodium hydroxide solution were heated in a 100 ml beaker in a water bath at 60° C. Then 7 g of ascorbyl palmitate were added, and the mixture was stirred with a magnetic stirrer until an almost clear solution was produced.

b) 385 g of glycerol were heated in a water bath at 60° C. and mixed with the solution prepared in a) while stirring slowly with a magnetic stirrer.

c) 22 g of crystalline β-carotene, 8 g of crystalline lycopene, 4 g of crystalline lutein, 5.6 g of OL-tocopherol and 166 g of fractionated coconut oil (Miglyol® 810, from Hüls, Troisdorf) were 2.4 heated in an oil bath, kept at 185° C. while stirring with a paddle stirrer over a period of 25 minutes, during which the carotenoids dissolved.

d) The solution prepared in c) was emulsified into the solution prepared in b) using a tooth-rimmed disperser (Ultraturrax®) over a period of 2 minutes. The resulting emulsion was cooled to 50° C. and then homogenized by passing once through a high-pressure homogenizer at 800 bar.

An emulsion with an average particle size of 0.2 μm and a carotenoid content of 5.0% by weight was obtained.

EXAMPLE 5

Production of a β-carotene/lycopene/lutein dry powder 600 g of crystalline β-carotene, 300 g of crystalline lycopene and 100 g of crystalline lutein were added under a nitrogen atmosphere to an aqueous solution of 584 g of gelatin (Bloom number 240) and 100 g of sodium ascorbate in 2800 g of degassed water. After the suspension had been ground in a ball mill for 1 hour, the finely ground suspension was added to a degassed aqueous solution of 1300 g of gelatin and 2044 g of sucrose. The solution additionally contained 9.5 g of ascorbyl palmitate as emulsifier and 14.3 g of tocopherol as antioxidant. The dispersion obtained after vigorous mixing was spray-dried in a manner known per se. A dry powder with a carotenoid content of 15% by weight was obtained.

We claim:

1. An oil containing dispersion comprising 5 to 35% by weight of a mixture of β-carotene, lycopene and lutein wherein the weight ratio of the mixture is 1 part of β-carotene, 0.05 to 20 parts of lycopene and 0.05 to 20 parts of lutein, and wherein the phosphorus content of the dispersion is less than 2.0% of the total weight of the mixture of β-carotene, lycopene and lutein.

2. An oil containing dispersion as claimed in claim 1, wherein the phosphorus content of the dispersion is less than 0.02% of the total weight of the mixture of β-carotene, lycopene and lutein.

3. An oil containing dispersion as claimed in claim 1, wherein β-carotene and lycopene are synthetically prepared.

4. An oil containing dispersion as claimed in claim 1, comprising a mixture of 1 part of β-carotene, 0.3 to 1.5 parts of lycopene and 0.1 to 0.5 parts of lutein.

5. An oil containing dispersion as claimed in claim 1, wherein the individual components used for the carotenoid mixture each have a purity of greater than 75% by weight.

6. An oil containing dispersion as claimed in claim 1, additionally comprising 0.01 to 40% by weight of one or more other active substances.

7. A food supplement, animal feed, human food or pharmaceutical or cosmetic preparation comprising an oil containing dispersion as defined in claim 1.

8. A soft gelatin capsule comprising an oil containing dispersion as defined in claim 1.

9. A soft gelatin capsule as claimed in claim 8, comprising 0.5 to 20 mg of β-carotene, 0.5 to 20 mg of lycopene and 0.5 to 20 mg of lutein.

* * * * *